(12) United States Patent
Markham et al.

(10) Patent No.: US 9,849,296 B2
(45) Date of Patent: Dec. 26, 2017

(54) DIRECTLY INTEGRATED FEEDTHROUGH TO IMPLANTABLE MEDICAL DEVICE HOUSING

(71) Applicant: Heraeus Deutschland GmbH & Co. KG, Hanau (DE)

(72) Inventors: Jacob Markham, Vadnais Heights, MN (US); Ulrich Hausch, Frankfurt (DE)

(73) Assignee: Heraeus Deutschland GmbH & Co. KG, Hanau (DE)

( * ) Notice: Subject to any disclaimer, the term of this patent is extended or adjusted under 35 U.S.C. 154(b) by 0 days.

(21) Appl. No.: 15/476,716

(22) Filed: Mar. 31, 2017

(65) Prior Publication Data

US 2017/0203107 A1    Jul. 20, 2017

Related U.S. Application Data

(62) Division of application No. 14/104,653, filed on Dec. 12, 2013, now Pat. No. 9,610,452.

(51) Int. Cl.
*A61N 1/375* (2006.01)
*C04B 37/02* (2006.01)
*B23K 1/00* (2006.01)

(52) U.S. Cl.
CPC .......... *A61N 1/3754* (2013.01); *B23K 1/0016* (2013.01); *C04B 37/026* (2013.01); *C04B 2237/125* (2013.01); *C04B 2237/403* (2013.01); *C04B 2237/708* (2013.01)

(58) Field of Classification Search
None
See application file for complete search history.

(56) References Cited

U.S. PATENT DOCUMENTS

| | | | |
|---|---|---|---|
| 3,065,533 A | 11/1962 | Dungan et al. | |
| 3,979,187 A | 9/1976 | Scherer | |
| 4,152,540 A | 5/1979 | Duncan et al. | |
| 4,217,137 A | 8/1980 | Kraska et al. | |
| 4,315,054 A | 2/1982 | Sack et al. | |
| 4,352,951 A | 10/1982 | Kyle | |
| 4,354,964 A | 10/1982 | Hing et al. | |

(Continued)

FOREIGN PATENT DOCUMENTS

| | | |
|---|---|---|
| DE | 69729719 | 7/2005 |
| DE | 102006054249 | 5/2008 |

(Continued)

OTHER PUBLICATIONS

Exner, Horst et al., "Laser Joining of Ceramics in Liquid Phase," pp. 1-8 (Nov. 8, 2011).

(Continued)

*Primary Examiner* — Erica Lee
(74) *Attorney, Agent, or Firm* — Dicke, Billig & Czaja, PLLC

(57) ABSTRACT

One aspect provides an implantable medical device with a housing having an opening with an opening width. A feedthrough is provided, including an insulator having a bottom surface and side surfaces and having an insulator width between opposing side surfaces that is greater than the opening width. A sinter joint is between at least one of the bottom surface, top surface, and side surfaces of the insulator and the housing which hermetically seals the insulator to the housing without an intervening ferrule.

17 Claims, 9 Drawing Sheets

(56) References Cited

U.S. PATENT DOCUMENTS

| | | | |
|---|---|---|---|
| 4,362,792 A | 12/1982 | Bowsky et al. |
| 4,456,786 A | 6/1984 | Kyle |
| 4,488,673 A | 12/1984 | Hopper, Jr. |
| 4,602,956 A | 7/1986 | Partlow et al. |
| 4,678,868 A | 7/1987 | Kraska et al. |
| 4,737,601 A | 4/1988 | Gartzke |
| 4,774,953 A | 10/1988 | Foote |
| 4,816,621 A | 3/1989 | Huebner et al. |
| 4,991,582 A | 2/1991 | Byers et al. |
| 4,992,910 A | 2/1991 | Evans |
| 5,043,535 A | 8/1991 | Lin |
| 5,046,262 A | 9/1991 | Kerbaugh |
| 5,245,999 A | 9/1993 | Dahlberg et al. |
| 5,272,283 A | 12/1993 | Kuzma |
| 5,333,095 A | 7/1994 | Stevenson et al. |
| 5,393,568 A * | 2/1995 | Valente .................... B05D 3/08 427/123 |
| 5,407,119 A | 4/1995 | Churchill et al. |
| 5,408,066 A | 4/1995 | Trapani et al. |
| 5,513,793 A | 5/1996 | Malmgren |
| 5,515,604 A | 5/1996 | Horine et al. |
| 5,587,111 A | 12/1996 | Watanabe et al. |
| 5,648,302 A | 7/1997 | Brow et al. |
| 5,654,106 A | 8/1997 | Purnell et al. |
| 5,683,435 A | 11/1997 | Truex et al. |
| 5,738,270 A | 4/1998 | Malmgren |
| 5,750,926 A | 5/1998 | Schulman et al. |
| 5,756,408 A | 5/1998 | Terashi et al. |
| 5,769,874 A | 6/1998 | Dahlberg |
| 5,782,891 A | 7/1998 | Hassler et al. |
| 5,796,019 A | 8/1998 | Lupton et al. |
| 5,821,011 A | 10/1998 | Taylor et al. |
| 5,851,222 A | 12/1998 | Taylor et al. |
| 5,855,711 A | 1/1999 | Araki et al. |
| 5,861,714 A | 1/1999 | Wei et al. |
| 5,866,851 A | 2/1999 | Taylor et al. |
| 5,870,272 A | 2/1999 | Seifried et al. |
| 5,905,627 A | 5/1999 | Brendel et al. |
| 6,031,710 A | 2/2000 | Wolf et al. |
| 6,093,476 A | 7/2000 | Horiuchi et al. |
| 6,232,004 B1 | 5/2001 | Lasater |
| 6,284,080 B1 | 9/2001 | Haq et al. |
| 6,414,835 B1 | 7/2002 | Wolf et al. |
| 6,579,492 B2 | 6/2003 | Wehler |
| 6,586,675 B1 | 7/2003 | Bealka et al. |
| 6,643,903 B2 | 11/2003 | Stevenson et al. |
| 6,660,116 B2 | 12/2003 | Wolf et al. |
| 6,999,818 B2 | 2/2006 | Stevenson et al. |
| 7,035,076 B1 | 4/2006 | Stevenson |
| 7,038,900 B2 | 5/2006 | Stevenson et al. |
| 7,068,491 B1 | 6/2006 | Burdon et al. |
| 7,107,099 B1 | 9/2006 | O'Phelan et al. |
| 7,136,273 B2 | 11/2006 | Stevenson et al. |
| 7,145,076 B2 | 12/2006 | Knappen et al. |
| 7,174,219 B2 | 2/2007 | Wahlstrand et al. |
| 7,174,223 B2 | 2/2007 | Dalton et al. |
| 7,222,419 B2 | 5/2007 | Horng et al. |
| 7,260,434 B1 | 8/2007 | Lim et al. |
| 7,274,963 B2 | 9/2007 | Spadgenske |
| 7,437,817 B2 | 10/2008 | Zhang et al. |
| 7,480,988 B2 | 1/2009 | Ok et al. |
| 7,502,217 B2 | 3/2009 | Zhao et al. |
| 7,561,917 B2 | 7/2009 | Wegrzyn, III et al. |
| 7,564,674 B2 | 7/2009 | Frysz et al. |
| 7,569,452 B2 | 8/2009 | Fu et al. |
| 7,630,768 B1 | 12/2009 | Coffed et al. |
| 7,668,597 B2 | 2/2010 | Engmark et al. |
| 7,706,124 B2 | 4/2010 | Zhao et al. |
| 7,720,538 B2 | 5/2010 | Janzig et al. |
| 7,736,191 B1 | 6/2010 | Sochor |
| 7,742,817 B2 | 6/2010 | Malinowski et al. |
| 7,747,321 B2 | 6/2010 | Fischbach et al. |
| 7,761,165 B1 | 7/2010 | He et al. |
| 7,765,005 B2 | 7/2010 | Stevenson |
| 7,794,256 B1 | 9/2010 | Sochor |
| 7,818,876 B2 | 10/2010 | Suaning |
| 7,901,761 B1 | 3/2011 | Jiang et al. |
| 7,930,032 B2 | 4/2011 | Teske et al. |
| 7,970,474 B2 | 6/2011 | Starke |
| 7,989,080 B2 | 8/2011 | Greenberg et al. |
| 8,000,804 B1 | 8/2011 | Wessendorf et al. |
| 8,065,009 B2 | 11/2011 | Biggs |
| 8,131,369 B2 | 3/2012 | Taylor et al. |
| 8,131,376 B1 | 3/2012 | Faraji et al. |
| 8,155,743 B2 | 4/2012 | Rundle et al. |
| 8,163,397 B2 | 4/2012 | Ok et al. |
| 8,179,658 B2 | 5/2012 | Brendel et al. |
| 8,189,333 B2 | 5/2012 | Foster |
| 8,288,654 B2 | 10/2012 | Taylor et al. |
| 8,346,362 B2 | 1/2013 | Kinney et al. |
| 8,355,785 B1 | 1/2013 | Hammond et al. |
| 8,391,983 B2 | 3/2013 | Lim |
| 8,494,635 B2 | 7/2013 | Troetzschel et al. |
| 8,497,435 B2 | 7/2013 | Nagata et al. |
| 8,528,201 B2 | 9/2013 | Troetzschel et al. |
| 8,552,311 B2 | 10/2013 | Koester et al. |
| 8,656,736 B2 | 2/2014 | Terao |
| 8,659,870 B2 | 2/2014 | Brendel et al. |
| 8,742,268 B2 | 6/2014 | Reisinger et al. |
| 8,755,887 B2 | 6/2014 | Troetzschel et al. |
| 8,825,162 B2 | 9/2014 | Reisinger |
| 8,886,320 B2 | 11/2014 | Troetzschel et al. |
| 8,894,914 B2 | 11/2014 | Pavlovic |
| 8,929,987 B2 | 1/2015 | Troetzschel et al. |
| 9,504,841 B2 | 11/2016 | Markham et al. |
| 9,610,451 B2 | 4/2017 | Markham et al. |
| 9,610,452 B2 | 4/2017 | Markham et al. |
| 2001/0013756 A1 | 8/2001 | Mori et al. |
| 2001/0018012 A1 | 8/2001 | Harmand et al. |
| 2001/0041227 A1 | 11/2001 | Hislop |
| 2002/0166739 A1 | 11/2002 | Naerheim |
| 2003/0109903 A1 | 6/2003 | Berrang et al. |
| 2003/0123215 A1 | 7/2003 | Allen et al. |
| 2004/0023101 A1 | 2/2004 | Jacobson et al. |
| 2004/0116976 A1 | 6/2004 | Spadgenske |
| 2004/0128016 A1 | 7/2004 | Stewart |
| 2006/0025866 A1 | 2/2006 | Serafin, Jr. et al. |
| 2006/0247714 A1 | 11/2006 | Taylor et al. |
| 2006/0259093 A1 | 11/2006 | Stevenson et al. |
| 2007/0041164 A1 | 2/2007 | Greenberg et al. |
| 2007/0183118 A1 | 8/2007 | Fu et al. |
| 2007/0217121 A1 | 9/2007 | Fu et al. |
| 2007/0276389 A1 | 11/2007 | Franke et al. |
| 2008/0060834 A1 | 3/2008 | Eck et al. |
| 2008/0071313 A1 | 3/2008 | Stevenson et al. |
| 2008/0119906 A1 | 5/2008 | Starke |
| 2008/0203917 A1 | 8/2008 | Maya |
| 2008/0269831 A1 | 10/2008 | Erickson |
| 2009/0079517 A1 | 3/2009 | Iyer |
| 2009/0192578 A1 | 7/2009 | Biggs |
| 2009/0281586 A1 | 11/2009 | Lim |
| 2009/0309459 A1 | 12/2009 | Ogashiwa et al. |
| 2010/0022861 A1 | 1/2010 | Cinbis et al. |
| 2010/0023086 A1 | 1/2010 | Lim |
| 2010/0109966 A1 | 5/2010 | Mateychuk et al. |
| 2010/0121438 A1 | 5/2010 | Jarvik |
| 2010/0241206 A1 | 9/2010 | Truex et al. |
| 2010/0258342 A1 | 10/2010 | Parker |
| 2011/0032658 A1 | 2/2011 | Iyer |
| 2011/0034965 A1 | 2/2011 | Troetzschel et al. |
| 2011/0034966 A1 | 2/2011 | Troetzschel et al. |
| 2011/0048770 A1 | 3/2011 | Reiterer et al. |
| 2011/0094768 A1 | 4/2011 | Davis et al. |
| 2011/0106228 A1 | 5/2011 | Reiterer et al. |
| 2011/0186349 A1 | 8/2011 | Troetzschel et al. |
| 2011/0190885 A1 | 8/2011 | Troetzschel et al. |
| 2011/0232961 A1 | 9/2011 | Teske |
| 2011/0232962 A1 | 9/2011 | Teske |
| 2012/0006576 A1 | 1/2012 | Barry et al. |
| 2012/0127627 A1 | 5/2012 | Brendel et al. |
| 2012/0193117 A1 | 8/2012 | Specht et al. |
| 2012/0193118 A1* | 8/2012 | Kempf .................. A61N 1/3754 174/50.53 |
| 2012/0193119 A1 | 8/2012 | Kempf et al. |

(56) References Cited

U.S. PATENT DOCUMENTS

| | | | |
|---|---|---|---|
| 2012/0193125 | A1 | 8/2012 | Pavlovic et al. |
| 2012/0193141 | A1 | 8/2012 | Reisinger et al. |
| 2012/0194981 | A1 | 8/2012 | Kempf et al. |
| 2012/0197326 | A1 | 8/2012 | Pavlovic |
| 2012/0197327 | A1 | 8/2012 | Specht |
| 2012/0197335 | A1 | 8/2012 | Reisinger |
| 2012/0197368 | A1 | 8/2012 | Reisinger |
| 2012/0200011 | A1 | 8/2012 | Pavlovic |
| 2012/0203294 | A1 | 8/2012 | Troetzschel |
| 2012/0319319 | A1 | 12/2012 | Parker et al. |
| 2013/0035733 | A1 | 2/2013 | Breyen et al. |
| 2013/0060312 | A1 | 3/2013 | Iyer et al. |
| 2013/0070387 | A1 | 3/2013 | Stevenson et al. |
| 2013/0127567 | A1 | 5/2013 | Iyer et al. |
| 2013/0138186 | A1 | 5/2013 | Iyer et al. |
| 2013/0138187 | A1 | 5/2013 | Iyer et al. |
| 2013/0184796 | A1 | 7/2013 | Marzano et al. |
| 2013/0184797 | A1 | 7/2013 | Tang et al. |
| 2013/0286536 | A1 | 10/2013 | Iyer et al. |
| 2013/0299233 | A1 | 11/2013 | Troetzschel et al. |
| 2014/0008121 | A1 | 1/2014 | Troetzschel et al. |
| 2014/0144014 | A1 | 5/2014 | Troetzschel et al. |
| 2014/0262494 | A1 | 9/2014 | Reisinger et al. |
| 2014/0318956 | A1* | 10/2014 | Okamoto ............ C04B 35/645 204/298.13 |
| 2014/0345934 | A1 | 11/2014 | Markham et al. |
| 2014/0368298 | A1 | 12/2014 | Reisinger |
| 2014/0371835 | A1 | 12/2014 | Powell et al. |
| 2015/0165218 | A1 | 6/2015 | Markham et al. |
| 2015/0165219 | A1 | 6/2015 | Markham et al. |
| 2015/0165220 | A1 | 6/2015 | Markham et al. |
| 2017/0071542 | A1 | 3/2017 | Markham et al. |

FOREIGN PATENT DOCUMENTS

| | | |
|---|---|---|
| DE | 102008021064 | 10/2009 |
| DE | 102009035971 | 2/2011 |
| DE | 102009035972 | 4/2011 |
| DE | 102010006837 | 8/2011 |
| DE | 102010006838 | 8/2011 |
| DE | 102010006689 | 9/2011 |
| DE | 102010006690 | 9/2011 |
| DE | 102011119125 | 5/2013 |
| EP | 0877400 | 11/1998 |
| EP | 0916364 | 5/1999 |
| EP | 1685874 | 8/2006 |
| EP | 1754511 | 2/2007 |
| EP | 2398026 | 12/2011 |
| WO | 03073450 | 9/2003 |
| WO | 2004110555 | 12/2004 |
| WO | 2008103166 | 8/2008 |
| WO | 2010091435 | 8/2010 |
| WO | 2011053540 | 5/2011 |
| WO | 2012110242 | 8/2012 |
| WO | 2012110245 | 8/2012 |
| WO | 2013075797 | 5/2013 |

OTHER PUBLICATIONS

Hussain, et al., "Electrical conductivity of an insulator matrix (alumina) and conductor particle (molybdenum) composites", Journal of the European Ceramic Society, vol. 23, Issue 2, Feb. 2003, pp. 315-321.

Gil et al., "Grain Growth Kinetics of Pure Titanium," Scripta Metallurgica et Materialia, vol. 33, No. 8, pp. 1361-1366 (1995).

The International Search Report and the Written Opinion for International Application No. PCT/IB2014/066773 dated Mar. 31, 2015 (12 pages).

The International Search Report and the Written Opinion for International Application No. PCT/IB2014/066774 dated May 6, 2015 (13 pages).

The International Search Report and the Written Opinion for International Application No. PCT/IB2014/066775 dated Feb. 19, 2015 (12 pages).

The Restriction Requirement for U.S. Appl. No. 14/104,636 dated Apr. 17, 2015 (5 pages).

The Office Action for U.S. Appl. No. 14/104,636 dated Jul. 20, 2015 (36 pgs).

Bulletin of Alloy Phase Diagrams, 1980, vol. 1, No. 2, p. 51-54.

The Final Office Action for U.S. Appl. No. 14/104,636 dated Dec. 7, 2015 (25 pages).

Alloy Data, Ti-6AI-4V, Carpenter technology corp., 2000, p. 1-2.

The Advisory Action for U.S. Appl. No. 14/104,636 dated Feb. 18, 2016 (4 pages).

The Office Action for U.S. Appl. No. 14/104,636 dated Jul. 8, 2016 (15 pages).

The Final Office Action for U.S. Appl. No. 14/104,636 dated Nov. 9, 2016 (12 pages).

The Restriction Requirement for U.S. Appl. No. 14/104,644 dated Jun. 3, 2015 (7 pages).

The Office Action for U.S. Appl. No. 14/104,644 dated Jul. 31, 2015 (29 pgs).

The Final Office Action for U.S. Appl. No. 14/104,644 dated May 5, 2016 (13 pages).

The Notice of Allowance for U.S. Appl. No. 14/104,644 dated Aug. 18, 2016 (11 pages).

The Restriction Requirement for U.S. Appl. No. 14/104,653 dated Jun. 26, 2015 (7 pages).

The Office Action for U.S. Appl. No. 14/104,653 dated Sep. 10, 2015 (46 pages).

The Final Office Action for U.S. Appl. No. 14/104,653 dated May 17, 2016 (21 pages).

The Notice of Allowance for U.S. Appl. No. 14/104,636 dated Jan. 23, 2017 (6 pgs).

The Notice of Allowance for U.S. Appl. No. 14/104,653 dated Jan. 18, 2017 (11 pgs).

The Office Action for U.S. Appl. No. 15/363,886 dated Apr. 7, 2017 (37 pgs).

\* cited by examiner

DIRECTLY INTEGRATED FEEDTHROUGH TO IMPLANTABLE MEDICAL DEVICE HOUSING

CROSS-REFERENCE TO RELATED APPLICATIONS

This application is a divisional of U.S. patent application Ser. No. 14/104,653, filed on Dec. 12, 2013, entitled "DIRECT INTEGRATION OF FEEDTHROUGH TO IMPLANTABLE MEDICAL DEVICE HOUSING BY SINTERING," now U.S. Pat. No. 9,610,452, to be issued Apr. 4, 2017, which is incorporated herein by reference.

This Patent Application is related to Ser. No. 14/104,636, filed on Dec. 12, 2013, entitled "DIRECT INTEGRATION OF FEEDTHROUGH TO IMPLANTABLE MEDICAL DEVICE HOUSING USING A GOLD ALLOY," now U.S. Pat. No. 9,610,451 to be issued Apr. 4, 2017, and U.S. Pat. No. 9,504,841, issued Nov. 29, 2016, entitled "DIRECT INTEGRATION OF FEEDTHROUGH TO IMPLANTABLE MEDICAL DEVICE HOUSING WITH ULTRASONIC WELDING," all of which are incorporated herein by reference.

BACKGROUND

Implantable medical devices, such as cardiac pacemakers, cardiac defibrillators, and neurostimulators, receive and/or deliver electrical signals to/from portions of the body via sensing and/or stimulating leads. Implantable medical devices typically include a metal housing (typically titanium) having a hermetically sealed interior space which isolates the internal circuitry, connections, power sources, and other device components from body fluids. A feedthrough device (often referred to simply as a feedthrough) establishes electrical connections between the hermetically sealed interior space and the exterior bodily fluid side of the device.

Feedthroughs typically include an insulator (typically ceramic) and electrical conductors or feedthrough pins which extend through the insulator to provide electrical pathways between the exterior and the hermetically sealed interior. A frame-like metal ferrule is disposed about a perimeter surface of the insulator, with the ferrule and insulator typically being joined to one another via a brazing or soldering process. The ferrule is configured to fit into a corresponding opening in the metal housing, with the ferrule being mechanically and hermetically attached to the housing, typically via laser welding. The insulator electrically insulates the feedthrough pins from one another and from the metal ferrule/housing.

The ferrule is typically joined to insulator via a welding or brazing process. However, the high temperatures employed by such processes heats the titanium of the housing about the perimeter of the opening to levels that cause a structural change in the titanium, commonly referred to as "grain growth". This structural change can distort the dimensions of the opening and cause the titanium about the perimeter of the opening to become less rigid, each of which can result in a weaker joint between the ferrule and the housing.

Additionally, machining the ferrule (typically from pure titanium) to provide a high tolerance gap between the ferrule and the insulator (about 10-50 μm) which is necessary to achieve a quality braze joint is demanding and costly. Furthermore, if the gap is not maintained during the brazing process, or if the brazing process itself is not properly performed, a weak joint may be formed that can lead to premature failure of the implantable device.

For these and other reasons there is a need for the embodiments of the present disclosure.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION

Figure 1:
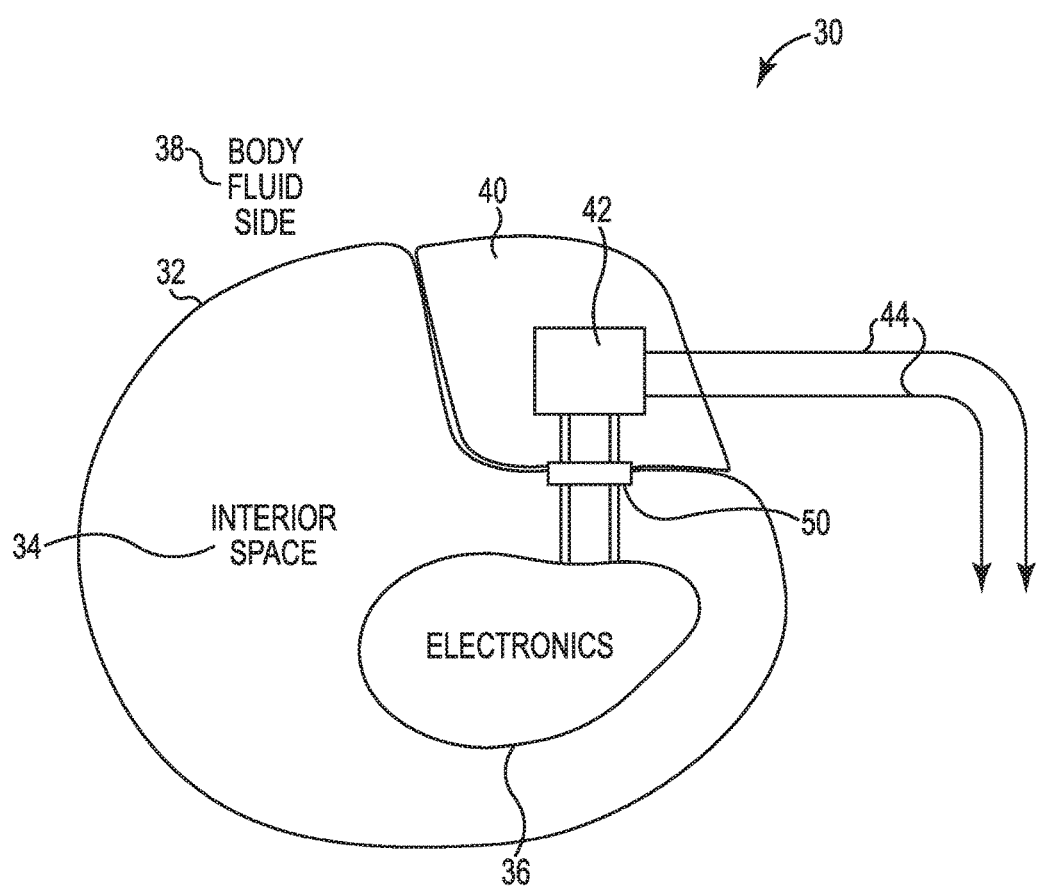
FIG. 1 generally illustrates an example of an implantable medical device according to one embodiment.

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

It is to be understood that the features of the various exemplary embodiments described herein may be combined with each other, unless specifically noted otherwise.

In accordance with one embodiment of the present disclosure, a method of attaching a feedthrough to a titanium housing of an implantable medical device is provided. The method includes applying a sinter paste onto a surface of the housing about a perimeter of an opening through the housing, the sinter paste including a biocompatible bonding material. An insulator of the feedthrough is placed onto the sinter paste so as to cover the opening, and the sinter paste is heated to a temperature less than a beta-transus temperature the titanium of the housing and to a temperature less than a melting point of the biocompatible bonding material for a desired duration to form, from the sinter paste, a sinter joint which bonds the feedthrough to the housing and hermetically seals the opening. According to one embodiment, portions of surfaces of the insulator contacting the sinter paste and resulting sinter joint are metallized.

Embodiments described herein for sintering the insulator of a feedthrough device directly to the device housing provides advantages over known processes of attaching a feedthrough device to device housing. First, attaching the feedthrough directly to the housing using a sinter joint eliminates the need for a ferrule (such as ferrule 56 of FIG. 2). By directly integrating the feedthrough to the housing via a sinter joint, as opposed to conventional techniques which integrate the feedthrough to the housing using a ferrule, the shortcomings associated with such a ferrule (e.g. brazed/welded joint, machining requirements, costs) are eliminated. Additionally, when combined with the use of cermet for conductive elements of the feedthrough, the present disclosure provides a feedthrough which is completely devoid of welds and/or brazing.

Additionally, by using a sintering process as described herein at temperatures below the β-transus temperature of titanium of the device housing, grain growth within the titanium material of the housing is greatly reduced relative to conventional techniques which employ high-temperature brazing or welding processes to attach feedthrough devices to housings via a ferrule, particularly in the region of the housing about a perimeter of an opening in which the feedthrough is disposed. In one embodiment, the temperature does not exceed 750° C. In one embodiment, the temperature does not exceed 350° C. Reducing the grain growth of the titanium of housing reduces dimensional distortions of housing as compared to conventional techniques, at least to levels within design tolerances, thereby providing stronger and more consistent hermetic seals between the insulator and the housing.

According to one embodiment, the sinter paste is formed by mixing the biocompatible bonding material in a powdered form with a binder material. In one embodiment, the powdered biocompatible bonding material has particles with a maximum dimension of less than 20 μm. In one embodiment, the particles are spherical in shape with a diameter less than 20 μm. In one embodiment, the biocompatible bonding material comprises gold. In one embodiment, the biocompatible bonding material comprises one of gold, platinum, palladium, and any alloy combination thereof.

According to one embodiment, the method includes applying a force to the feedthrough during the heating to push the insulator toward the housing so as to compress the sinter paste as the sinter paste loses volume due to binders within the sinter paste burning off during the heating, thereby providing a stronger joint and hermetic seal. In one embodiment, a counter force is provided to support the housing to prevent deflection of the housing. In one embodiment, the heating is carried out in an oven having a non-oxygen and non-vacuum environment to enable the melted sinter material to flow and to prevent oxidation of the titanium material of the housing, thereby enabling a stronger joint and improved hermetic seal.

Another aspect provides an implantable medical device including a housing having an opening with an opening width, and a feedthrough including an insulator having a bottom surface and side surfaces and having an insulator width between opposing side surfaces that is greater than the opening width. A sinter joint between at least one of the bottom surface, top surface, and side surfaces of the insulator and the housing hermetically seals the insulator to the housing.

In one embodiment, a width of the sinter joint between the insulator and the housing along a perimeter of the housing opening is at least one quarter a width of the insulator at its widest point. In one embodiment, the housing includes a flange which forms a recess about the opening, the opening being disposed at a bottom of the recess, and the insulator being positioned at least partially within the recess and over the opening. In one embodiment, a plane normal to the opening passes through the housing, the sinter joint, and the insulator. In one embodiment, the sinter joint has a thickness in a direction perpendicular to the housing in a range from 25 to 200 μm.

In one embodiment, the sinter joint comprises gold. In one embodiment, the sinter joint comprises one of gold, palladium, iridium, and alloy combinations thereof. In one embodiment, the sinter joint has a density of not more than 99 percent of the biocompatible bonding material. In one embodiment, the sinter joint has a density in a range from 90 to 99 percent of the biocompatible bonding material. In one embodiment, the housing comprises titanium, and wherein the titanium has an average grain size of not more than 100 μm.

A further aspect of the present disclosure provides a method of attaching a feedthrough device to hermetically seal an opening in a titanium housing of an implantable medical device. A sinter paste is applied about a perimeter of the opening, the sinter paste including a biocompatible bonding material, and a feedthrough is positioned on the sinter paste to cover the opening, the feedthrough having a width greater than a width of the opening. The sinter paste is heated to a temperature less than a β-transus temperature of the titanium of the housing and less than a melting point of the biocompatible bonding material for a duration which to limit an average grain size of the titanium to not greater than 100 μm and to form a sinter joint from the sinter paste that bonds the feedthrough to the housing and hermetically seals the opening. As described above, by reducing the grain growth of the titanium of housing relative to conventional processes, which result in grain sizes well in excess of 100 μm (for example, greater than 300 μm), dimensional distortions of housing are reduced as compared to conventional techniques, at least to levels within design tolerances, thereby providing stronger and more consistent hermetic seals between the insulator and the housing.

In one embodiment, the method includes forming the sinter paste by mixing the biocompatible bonding material in a powder form with a binding material. In one embodiment, the method includes applying a force to the feedthrough during the heating to push the insulator toward the housing so as to compress the sinter paste as the sinter paste loses volume due to binders within the sinter paste burning off during the heating, and providing a counter force to support the housing to prevent deflection of the housing.

FIG. 1 is a block and schematic diagram generally illustrating one embodiment of an implantable medical device 30, such as a cardiac pacemaker for example. Implantable medical device 30 includes a hermetically sealed metal case our housing 32, typically formed of titanium, which defines a hermetically sealed interior space 34 in which device electronics 36 are disposed and protected from fluids of the body fluid side 38 external to housing 32. A header 40 attaches to housing 32 and includes a connector block 42 which typically includes one or more sockets for connecting to one or more sensing and/or stimulating leads 44 that extend between implantable medical device 30 and desired regions of the body, such as the human heart and brain, for example. A feedthrough device 50 establishes electrical pathways or connections through housing 32 that maintain the integrity of hermetically sealed interior space 34 and provide electrical connection of leads 44 to internal device electronics 36.

Figure 2:
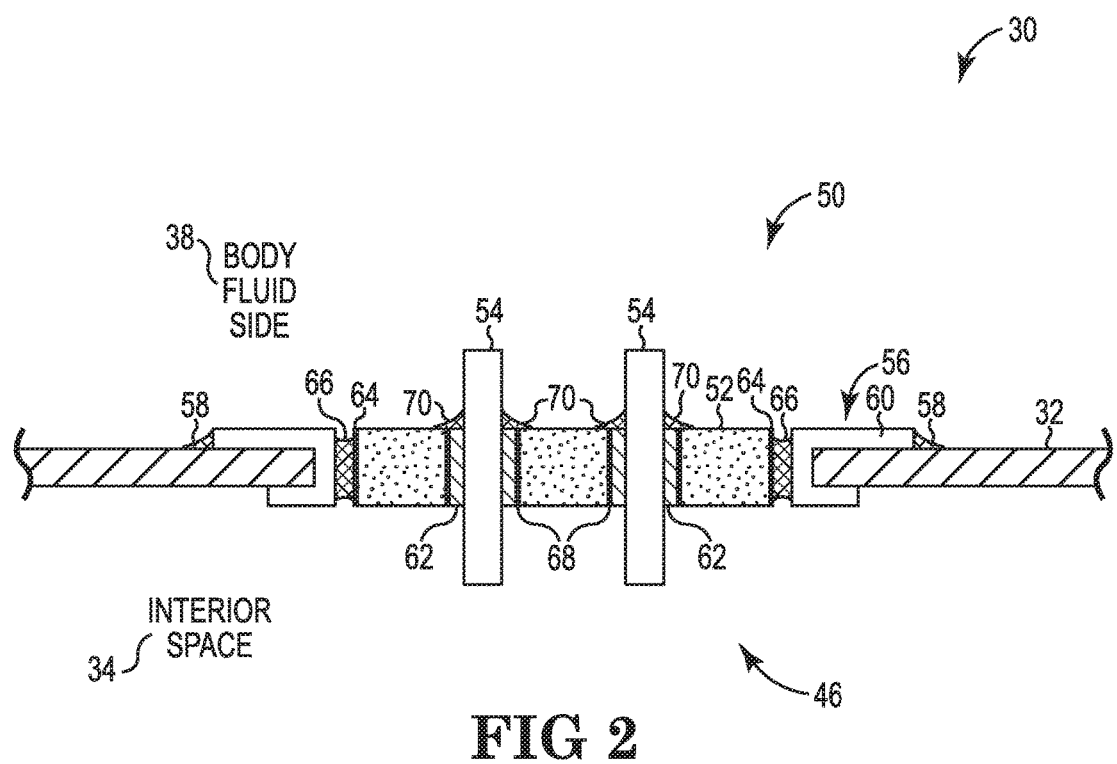
FIG. 2 illustrates a feedthrough device in an implantable in accordance with the prior art.

FIG. 2 is a cross-sectional view illustrating portions of an implantable medical device, such as medical device 30 of FIG. 1, including metal housing 32 having an opening 46 in which a conventional feedthrough device 50 is positioned. Feedthrough device 50 includes an insulator 52, feedthrough pins or conducting elements 54, and a ferrule 56. A ferrule 56, comprising a frame-like metal structure, holds insulator 52 and which is configured to fit into opening 46 for attachment to housing 32. Ferrule 56 is a bio-compatible material, typically titanium, which is mechanically and hermetically attached to housing 32 by laser welds 58, or similar techniques. Ferrule 56, as illustrated in FIG. 2, sometimes includes a flange 60 to further aid in securing ferrule 56 to housing 32.

Conducting elements 54 extend through openings or vias 62 in insulator 52 and are formed of an electrically conductive material so as to provide electrically conductive pathways from the external body fluid side 38 of housing 32 to hermetically sealed interior space 34. Insulator 52 is formed of a non-electrically conductive material, such as a ceramic material, aluminum oxide ($Al_2O_3$) for example, and electrically isolates conducting elements 54 from one another and from ferrule 56 and housing 32.

When attaching insulator 52 and ferrule 56 to one another, a perimeter surface of insulator 52 is typically metalized (through a sputter coating process, for example) to provide a thin metal coating 64 thereon. Ferrule 56 is then joined to insulator 52 via metal coating 64 using a braze 66, such as of gold, for example, to form a biocompatible and hermetic seal. Similarly, interior surface of vias 62 are provided with a metal coating 68 and a braze 70 (e.g. gold) is used to couple conducting elements 54 to insulator 52 and form a biocompatible and hermetic seal.

In order to achieve a quality braze, and thereby a quality hermetic seal, a proper gap must be maintained between ferrule 56 and insulator 52 during the brazing process (typically about 10-50 µm) so that the brazing material (e.g. gold) is properly drawn into the gap by capillary action to create a strong and reliable braze 66. Forming ferrule 56, typically via machining processes, to meet the tight tolerances required to provide the proper gap with insulator 52 as well as to the dimensions of opening 46 in housing 42 is time consuming and costly. Also, during the brazing process, intermetallics are formed between the brazing material (e.g. gold) and the material (e.g. titanium) of ferrule 56, with the intermetallics being brittle as compared to the brazing material. If the gap between ferrule 56 and insulator 52 is too small, the amount of intermetallics may be large relative to the amount of pure brazing material (e.g. gold) resulting in a brittle braze 66 that may crack and comprise the hermetic seal.

Additionally, heat from the brazing (or welding) of ferrule 56 to housing 32 can cause structural changes in the titanium of housing 32 about opening 46 (and to ferrule 56) due to "grain growth" in the titanium. Such "grain growth" can cause undesirable dimensional changes in opening 46 and can cause the titanium about the perimeter of opening 46 to become less rigid (i.e. more flexible), which such changes leading to a weakened or defective joint.

All polycrystalline materials, including titanium, are made of closely packed atoms, with "regions of regularity" within these closely packed atoms (i.e. where the atoms have a regular structure, such as 8-co-ordination and 12-co-ordination, for example) being referred to as "crystal grains". Metal consists of a vast number of these crystal grains. The boundaries of these crystals (i.e. "grain boundaries") are locations at which atoms have become misaligned (i.e. the regular structure is discontinuous). Metals having smaller grains and, thus, more grain boundaries, are harder than metals having larger grains, which have fewer grain boundaries and, as a result, are softer and more flexible.

Heating of a metal, such as titanium, causes the atoms to move into a more regular arrangement, thereby decreasing the overall number of crystal grains but increasing the grain size of the remaining grains (i.e. the number of grains per unit volume decreases). The process by which the average grain size increases, so-called "grain growth", rearranges the crystalline structure of the metal and can cause dimensional changes (i.e. dimensional deformation) of the metal and cause the metal to become more flexible.

Titanium has an α-phase, which has a close-packed hexagonal crystal structure, and a β-phase, which has centered-cubic crystal structure and that is more open and prone to grain growth than the hexagonal structure. Titanium transitions from α-phase to β-phase, the so-called β-transus, when heated to or above a certain temperature, referred to as the β-transus temperature. The β-transus temperature is affected by impurities in the titanium (e.g. iron, carbon, hydrogen), but typically occurs at about 880° C. in commercially-pure titanium. Commercially pure titanium, as opposed to titanium alloys having additive such as aluminum (Al), typically has a microstructure of primarily α-phase grains having an average grain size in the range of 10-40 µm.

The grain growth of a metal, including titanium, is a function of the time and temperature for which a metal is heated. For example, while the average grain size of commercially-pure titanium increases when heated to temperatures below the β-transus temperature, such grain growth accelerates rapidly when the the titanium is heated to a temperature at or above the β-transus temperature and the titanium transitions from α-phase to β-phase. For instance, the average grain size of commercially-pure titanium has been shown to increase in from about 10-40 µm to about 70 µm when heated at 700° C. for 120 minutes, to about 100 µm when heated at 750° C. for 120 minutes, and to about 180 µm when heated at 800° C. for 120 minutes. However, the average grain size of commercially-pure titanium has been shown to increase in from about 10-40 µm to about 350 µm when heated at 1000° C. for 120 minutes, and to about 425 µm when heated at 1100° C. for 120 minutes.

With reference to conventional feedthrough 50 of FIG. 2, attaching ferrule 56 to housing 32 by laser welding or brazing (e.g. gold braze) heats housing 32 to a temperature well above the β-transus temperature of titanium, resulting in rapid grain growth in the titanium of housing 32. For example, the average grain size may increase by 300 µm or more. Such grain growth causes dimensional distortions in housing 32 that can cause opening 46 to be outside of specified tolerances and causes the titanium about the perimeter of opening 46 to become less rigid, each of which can result in a poor or defective seal being formed between housing 32 and feedthrough 50.

Figure 3:
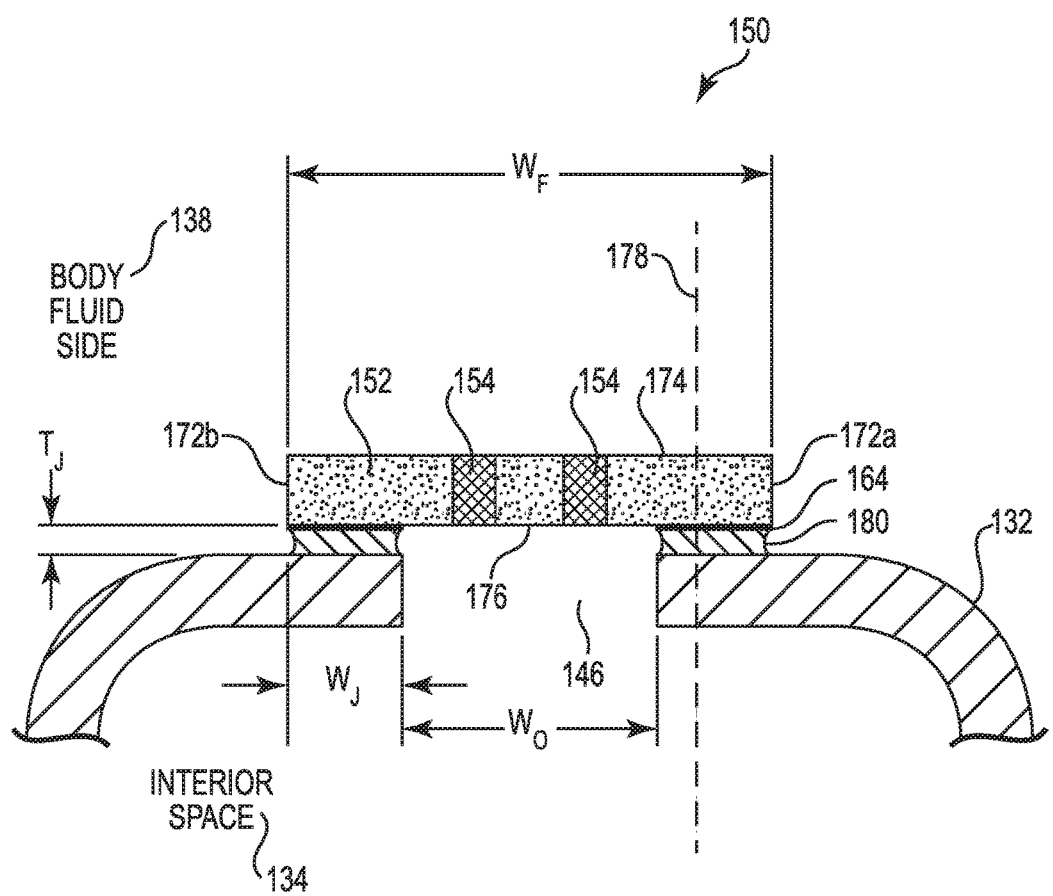
FIG. 3 illustrates a cross-sectional view of a feedthrough in an implantable medical device in accordance with one embodiment.

FIG. 3 is a schematic diagram illustrating portions of an implantable medical device 130 including a feedthrough 150 according to one embodiment of the present disclosure. Feedthrough 150 includes an insulator 152 and conducting elements 154 extending therethrough. As will be described in greater detail below, feedthrough 150 is attached directly to housing 132 via insulator 152 using a sinter joint 180 that is formed at low-temperatures, at least at temperatures below the β-transus temperature of the titanium of housing 132.

By attaching feedthrough 150 directly to housing 132 via insulator 152, the need for a ferrule (such as ferrule 56 of FIG. 2) is eliminated, thereby eliminating the cost of manufacturing such a ferrule as well as the difficulties and shortcomings associated with attaching such a ferrule to the insulator (such as insulator 52 of FIG. 2). Additionally, by attaching feedthrough 150 to housing 132 using sintering techniques at reduced temperatures relative to conventional welding or brazing techniques, dimensional distortions of housing 132 due to the high temperatures and grain growth of titanium are substantially reduced, at least to levels that maintain dimensions of housing 32 within specified tolerances, and the titanium remains in a more rigid state.

While FIG. 3 a cross-sectional view illustrating portions housing 132, particularly the location where feedthrough 150 attaches to housing 132 to seal opening 146, implantable medical device 130 may include additional features similar to those described with respect to medical device 30 of FIG. 1. According to one embodiment, housing 132 is formed of titanium and defines a sealed interior space 134 in which device electronics are disposed and protected from fluids of body fluid side 138 external to housing 132. According to one embodiment, a header, similar to header 40 of FIG. 1, for example, maybe also provided which attaches to housing 132 and includes a connector block having one or more sockets for connecting to one or more sensing and/or stimulating leads.

Similar to that described above with regard to FIG. 3, feedthrough 150 establishes electrical connections or pathways from body fluid side 138 to the interior space 134 of housing 132 while maintaining the integrity of hermetically sealed interior space 134 via conducting elements 154 which pass through insulator 152. According to one embodiment, insulator 152 is a glass or ceramic material, such as aluminum oxide ($Al_2O_3$). According to one embodiment, conducting elements 154 are formed of a cermet.

In the context of one embodiment, the terms, "cermet" or "cermet-containing," refers composite materials made of ceramic materials in a metallic matrix (binding agent). These are characterized by their particularly high hardness and wear resistance. The "cermets" and/or "cermet-containing" substances are cutting materials that are related to hard metals, but contain no tungsten carbide hard metal and are produced by powder metallurgical means. A sintering process for cermets and/or cermet-containing elements proceeds is the same as that for homogeneous powders, except that the metal is compacted more strongly at the same pressuring force as compared to the ceramic material. The cermet-containing bearing element has a higher thermal shock and oxidation resistance than sintered hard metals. In most cases, the ceramic components of the cermet are aluminum oxide ($Al_2O_3$) and zirconium dioxide ($ZrO_2$), whereas niobium, molybdenum, titanium, cobalt, zirconium, chromium and platinum are conceivable as metallic components.

According to one embodiment, such as illustrated by FIG. 3, the ceramic (e.g. $Al_2O_3$) of insulator 152 and the cermet of conducting elements 154 are formed in a first process such that an interface between insulator 152 and conducting elements 154 are hermetically sealed without the use of a braze or solder. According to one example of such an embodiment, the ceramic of insulator 152 is a multi-layer ceramic sheet into which a plurality of vias is introduced. The cermet of conducting elements 154 is then introduced into the vias. In one embodiment, both materials are introduced in a green state, and the combination is fired together. According to such an embodiment, the joining of insulator 152 with conducting elements 154 forms a hermetic seal without the use of braze or solder.

According to one embodiment, sinter joint 180 is formed of a biocompatible material, such as gold or a gold alloy, for example, which is applied as a sinter paste prior to the carrying out of a sintering process to form sinter joint 180 (with such process being described in greater detail below). According to one embodiment, the surfaces of insulator 152 at which sinter joint 180 is to be formed are provided with a metallized layer 164 using a suitable process, such as sputter coating or electroplating process, for example. According to one embodiment, metallized layer 164 comprises a biocompatible metal such as niobium, platinum, palladium, titanium, and gold, for example.

According to one embodiment, feedthrough 150 has a width $W_F$ at a widest point between opposing surfaces 172a, 172b, which is wider than a width $W_O$ of opening 146 in housing 132. Insulator 152 further includes an upper surface 174 and a lower surface 176. It is noted that feedthrough 150 is illustrated in vertical cross-section in FIG. 3, but in horizontal cross-section (i.e. between upper and lower surfaces 174 and 176) feedthrough 150 can be of a variety of shapes, such a circular, oval, and rectangular, for example. According to one embodiment, sinter joint 180 has a width $W_J$ and a thickness $T_J$. According to one embodiment, housing 132, feedthrough 150, and sinter joint 180 are disposed relative to another such that a line 178 drawn through at least a portion of feedthrough 150, wherein line 178 is orthogonal to upper surface 174 of feedthrough 150, passes through housing 132, sinter joint 180, and feedthrough 150.

According to one embodiment, sinter joint 150 is formed from a biocompatible material. According to one embodiment, sinter joint 150 is formed of one of gold, platinum, palladium, and any alloy combination thereof. According to one embodiment, the thickness $T_J$ of sinter joint 180 is in a range from 20 to 200 μm.

Figure 4:
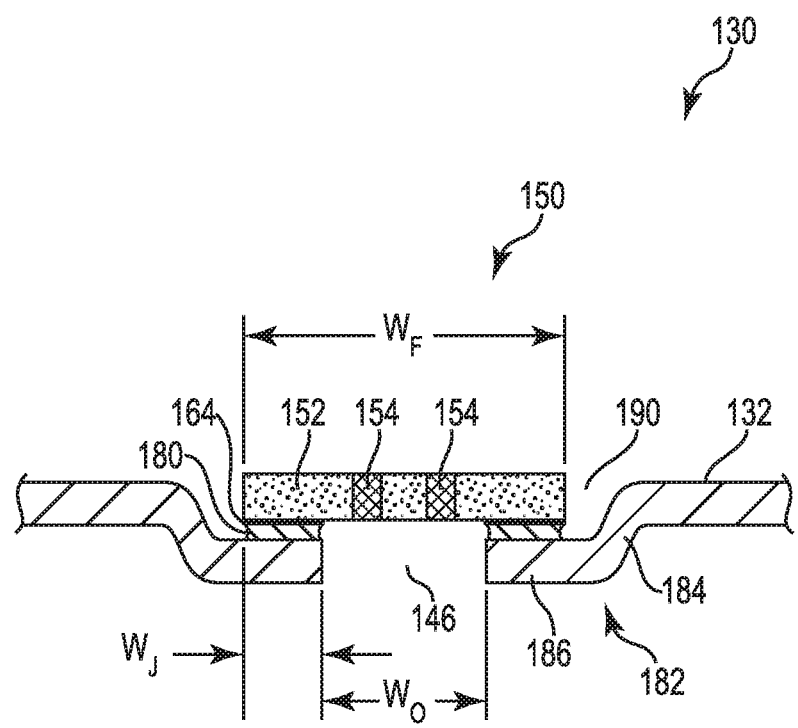
FIG. 4 is cross-sectional view illustrating a feedthrough in an implantable medical device including according to one embodiment.

FIG. 4 is schematic diagram illustrating implantable medical device 150 according to one embodiment of the present disclosure. According to the embodiment of FIG. 4, titanium housing 132 includes a flange 182 that forms a recess 190 in housing 132 about opening 146, with opening 146 disposed at the bottom of recess 190. According to one embodiment, as illustrated, flange 182 includes a downwardly angled portion 184 that forms a sidewall of recess 190 and transitions to a horizontal portion 186 that forms a bottom of recess 190 about a perimeter of opening 146. According to one embodiment, as illustrated, sinter joint 180 is formed between insulator 152 and horizontal portion 186 of flange 182 of housing 132.

Figure 5:
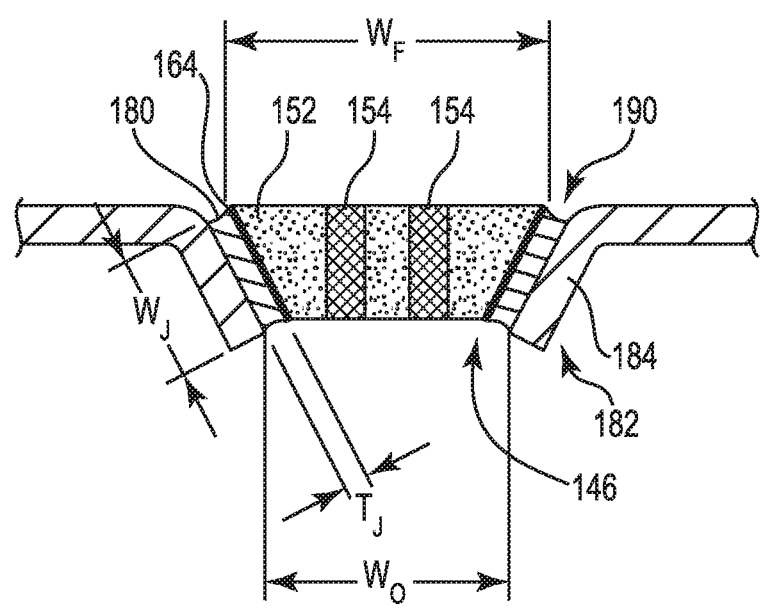
FIG. 5 is cross-sectional view illustrating a feedthrough in an implantable medical device including according to one embodiment.

FIG. 5 is schematic diagram illustrating implantable medical device 150 according to one embodiment of the present disclosure. According to the embodiment of FIG. 4, titanium housing 132 includes flange 182 which forms recess 190 in housing 132. However, unlike the embodiment of FIG. 4, flange 182 includes only a downwardly angled portion 184 and has no horizontal portion such that recess 190 is wider at the top than at the bottom and that an open bottom of recess 190 forms opening 146.

In the embodiments of FIGS. 4 and 5, flange 182 defines surfaces on which a sinter paste (see below) from which sinter joint 180 is formed is deposited, and defines recess 190 in which feedthrough 150 is seated. FIGS. 4 and 5 illustrate only two embodiments of any number of geometries which may be employed by flange 182 to form recess 190. According to one embodiment, the width $W_J$ of sinter joint 180 varies depending on a particular type of geometry employed by housing 132 at opening 146. For example, according to one embodiment, the width $W_J$ of the embodiment illustrated by FIG. 4 is at least one-fourth the width $W_F$ of feedthrough 150, while the width $W_J$ of the embodiment illustrated by FIG. 5 is at least one-half the width $W_F$ of feedthrough 150. As such, the ratio of the width $W_J$ of sinter joint 180 to the width $W_F$ of feedthrough 150 may vary depending on the geometry of housing 132 about opening 146.

Figure 6:
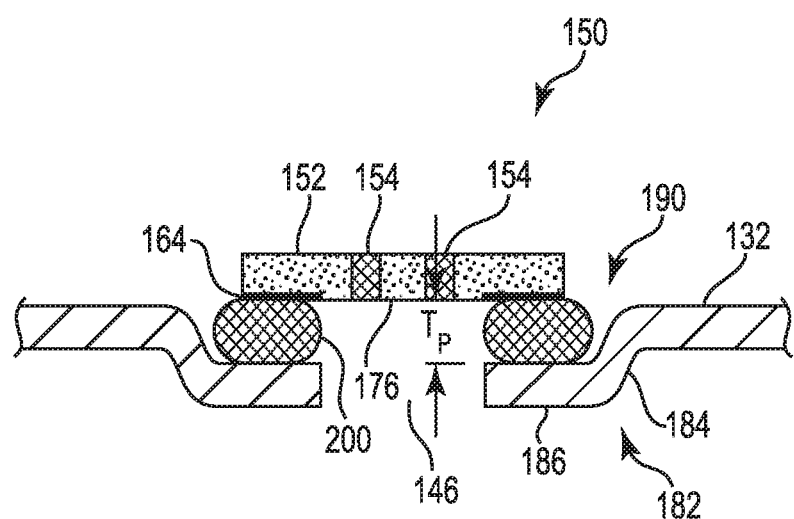
FIG. 6 is a block and schematic diagram illustrating a method of attaching a feedthrough to a housing using sintering process according to one embodiment.
Figure 7:
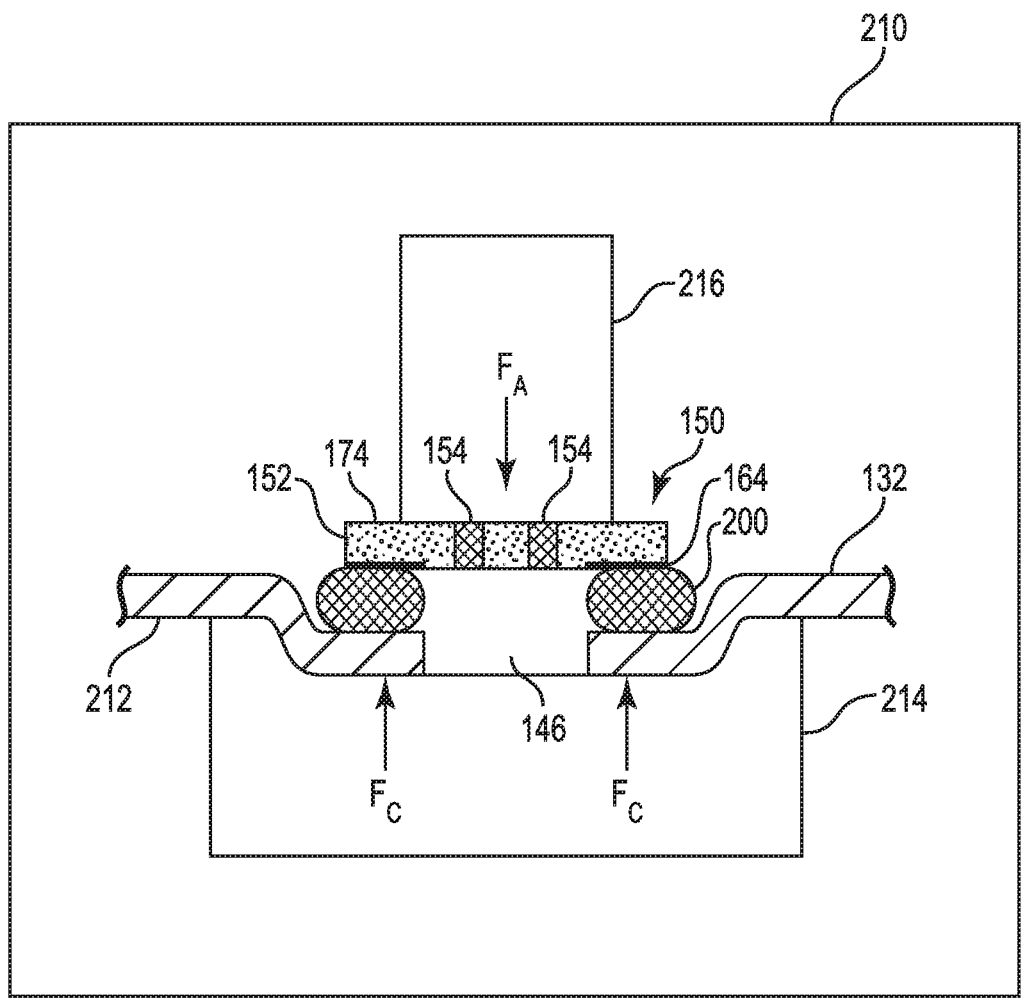
FIG. 7 is a feedthrough to a housing using sintering process according to one embodiment.
Figure 8:
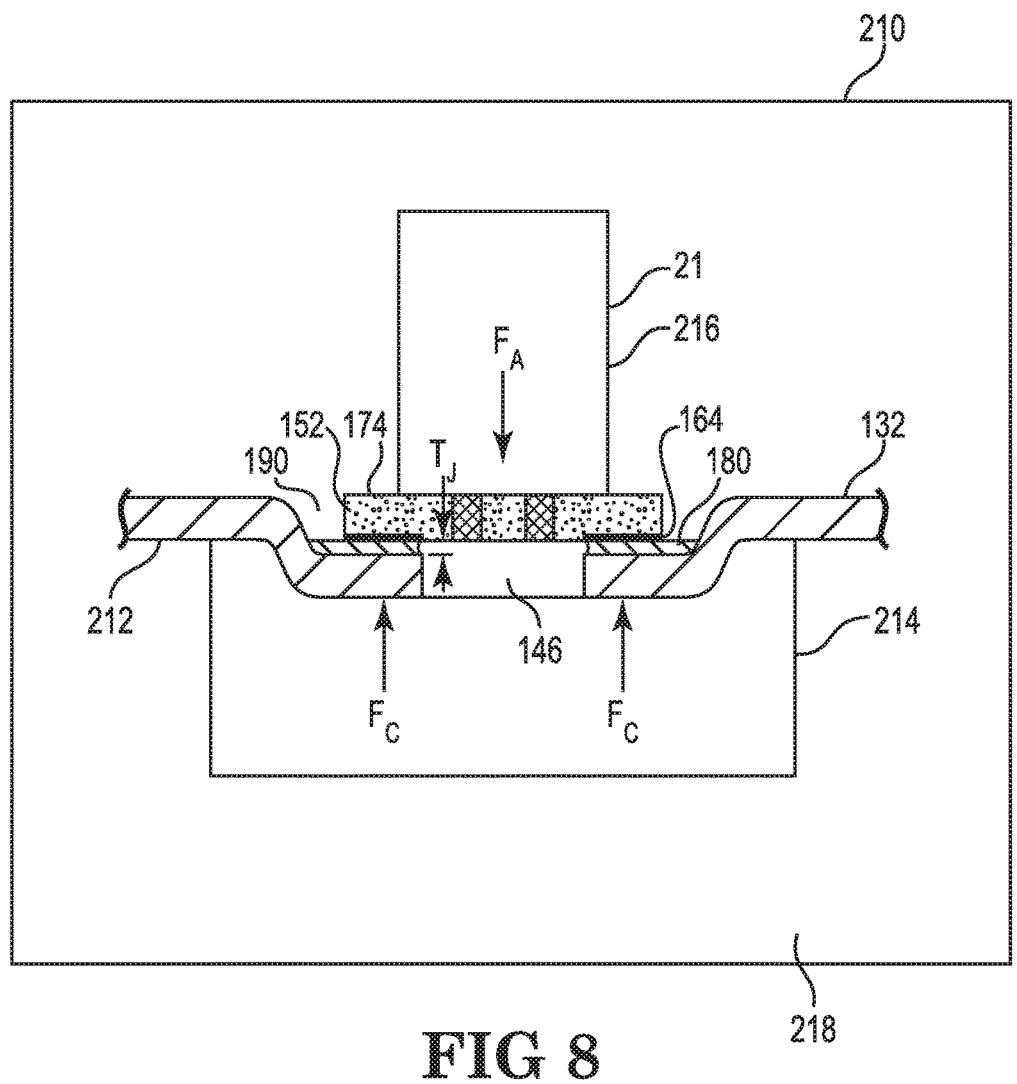
FIG. 8 is a feedthrough to a housing using sintering process according to one embodiment.

FIGS. 6 through 8 below illustrate and describe embodiments for low-temperature attachment of feedthrough 150 to housing 132 via sintering according to the present disclosure. Sintering is process whereby a solid object is formed from powders, such metal powders (e.g. the powdered bonding material of sinter paste 200), by heating, but not melting, the powder. A force is also sometimes applied to compress the powder during the heating process. As opposed to processes where materials are melted, sintering is based on the process of diffusion whereby the atoms in the particles diffuse across particle boundaries as a result of their kinetic energy of random motion, thereby fusing the particles together to form a single, solid piece. Diffusion will occur to some extent in any material above absolute zero, but takes place more rapidly at elevated temperatures.

With reference to FIG. 6, housing 132 of an implantable medical device is provided, such as implantable medical device 130 of FIG. 4, housing 132 including an integral flange 182 having angled and horizontal portions 184, 186 forming recess 190 about opening 146. A sinter paste 200 is applied within recess 190 about a perimeter of opening 146, with recess 190 serving to hold sinter paste 200 in position. As illustrated, sinter paste 200 is applied with a thickness $T_P$ that is greater than that of the thickness $T_J$ of the finished sinter joint 180 (see FIG. 4). According one embodiment, sinter paste 200 is applied to feedthrough 150 in lieu of housing 132. In one embodiment, sinter paste 200 is applied to both housing 132 and feedthrough 150.

According to one embodiment, sinter paste 200 includes a biocompatible bonding material in a fine powder or particle form mixed with a binder material. According to one embodiment, as described above, the powdered biocompatible bonding material includes one of gold, platinum, and palladium, or any combination thereof, for example. According to one embodiment, the particle size of the biocompatible bonding material does not exceed 20 μm. According to one embodiment, the particles of biocompatible bonding material are spherical in shape. According to one embodiment, the binder material includes organic solvents, such a butyl terpineol, butyl glycol, and butyl cellusolve, for example.

As will be described in greater detail below, the fine particle size enables sintering of the biocompatible bonding material of sinter paste 200 to occur at temperatures much lower than the melting points of the biocompatible bonding materials when in non-powdered form. For example, while the melting point of non-powdered gold is 1,064° C., the temperature at which the sintering effect will occur and cause the gold particles to fuse with one another is well below the 880° C. β-transus temperature of titanium. According to one embodiment, for example, the sintering of gold particles of sinter paste 200 occurs at 350° C.

According to the embodiment illustrated by FIG. 6, after application of sinter paste 200, feedthrough 150 is positioned within recess 190 with portions of bottom surface 176 of insulator 152 contacting sinter paste 200. According to one embodiment, as illustrated, at least the portions of bottom surface 176 contacting sinter paste 200 are provided with a metallized layer 164.

Referring to FIG. 7, after feedthrough 150 is positioned on sinter paste 200 so as to cover opening 146, housing 132 and feedthrough 150 are placed into an oven 210. According to one embodiment, a support 214 is provided to support a bottom surface 212 of housing 132, at least in a region of opening 146, and a weight or anvil 216 is placed on the upper surface 174 of feedthrough 150. Anvil 216 provides a force $F_A$ which pushes feedthrough 150 toward housing 132 and onto sinter paste 200, while support 214 provides a counter force $F_C$ to prevent deflection of housing 132 about opening 146 which might otherwise be caused by anvil 216.

At FIG. 8, after positioning housing 132 and feedthrough 150 within oven 210, oven 210 is heated to carry out the sintering process and form finished sinter joint 180 from sinter paste 200. According to one embodiment, sinter paste 200, together with housing 132 and feedthrough 150, are heated to a temperature below the β-transus temperature of the titanium of housing 132 (i.e. about 880° C.) for a desired duration until the finished sinter joint 180 is formed from sinter paste 200 so to arrive at the implantable medical device 130 illustrated by the embodiment of FIG. 4. According to one embodiment, oven 210 is heated to a temperature not exceeding 750° C.

As described above, although heated to a temperature below the melting point of the powdered bonding material of sinter paste 200 (e.g. the melting point of gold is 1,064° C.), the boundaries of the particles of the powdered bonding material of sinter paste 200 fuse together via the diffusion process to form single solid sinter joint 180. The smaller the particle size of the bonding material of sinter paste 200, the lower the temperature and the more quickly the diffusion process will occur. As described above, according to one embodiment, a largest dimension of the particles of the bonding material (e.g. a diameter when the particles are spherical) of sinter paste 200 does not exceed 20 μm.

As sinter paste 200 is heated, the binder material is burned off. For example, according to one embodiment, the organic solvents employed as a binder materials for sinter paste 200 (such as those listed above) are burned off at a temperature of approximately 150-160° C. As the binder material is burned off, the volume of sinter paste 200 begins to decrease. As the binder material is burned off, anvil 216 compresses the remaining material of sinter paste 200 into a denser form to ensure that good contact and fusion is made between the powder particles themselves, and between the powder particles and the metallized layer 164 and titanium of housing 132.

Oven 210 has a controlled interior environment 218. According to one embodiment, in order to enable binder materials of sinter paste 200 to burn off to form the final sinter joint 180, interior environment 218 is not a vacuum environment. According to one embodiment, in order to prevent oxidation of the titanium of housing 132, and possibly of metallized layer 164, which would inhibit the bonding of the binding materials of sinter paste 200 to such surfaces and result in a poor seal therebetween, interior environment 218 is a non-oxygen environment. According to one embodiment, interior environment 218 is one of helium and argon. According to one embodiment, interior environment 218 is one of hydrogen, helium, and argon.

Any number of scenarios are envisioned with regard to the heating of oven 210 in order to achieve an optimal sinter joint 180 between housing 132 and feedthrough 150, wherein heating parameters, such as temperature and duration, may vary depending on a variety of factors, such as the type of bonding materials and binder materials employed by sinter paste 200, on a thickness with which sinter paste 200 is applied to housing 132, and on a type of geometry employed about opening 146 (e.g. a shape of recess 190), for example.

For example, according to one embodiment, where sinter paste 200 employs gold particles as the biocompatible bonding material and organic solvent(s) as the binder material (such as described above), the heating of oven 210 to perform the sintering process includes multiple stages. In a first stage, the temperature is ramped up from an initial temperature of 30° C. to a temperature of 160° C. over a period of 30 minutes. In a second stage, the temperature is maintained at 160° C. for a period of 30 minutes to ensure that the binder materials in sinter paste 200 are completely burned off. In a third stage, the temperature is ramped up from 160° C. to 350° C. and held at 350° C. for a period of 60 minutes to ensure complete fusing (sintering) of the particles of bonding material of sinter paste 200, in this case gold particles. In a fourth stage, the temperature is ramped down from 350° C. to 30° C. over a period of 60 minutes. Housing 132, with feedthrough 150 bonded thereto by finished sinter joint 180, such as illustrated by FIG. 4, is then removed from oven 210. Again, it is noted that any number of heating scenarios may be employed which may include more or fewer than the four steps described by the above example embodiment.

Figure 9:
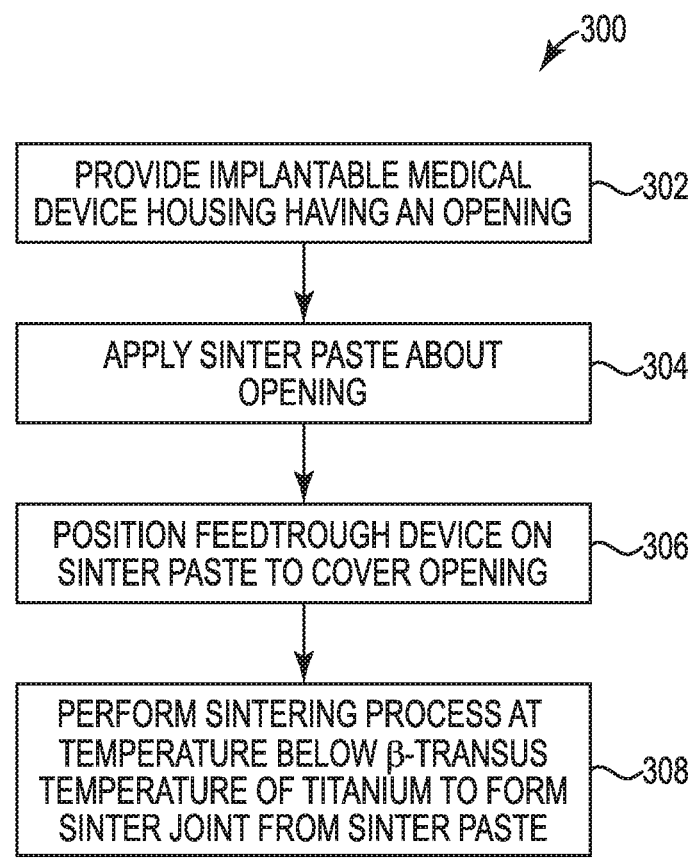
FIG. 9 is a flow diagram illustrating a method of attaching a feedthrough to a housing using sintering according to one embodiment.

FIG. 9 is a flow diagram illustrating a process 300 for hermetically attaching a feedthrough to a housing of an implantable medical device using a sinter joint according to one embodiment of the present disclosure. Process 300 begins at 302 where a titanium housing for an implantable medical device is provided, such as housing 132 of FIG. 3. According to one embodiment, housing 132 includes a flange which forms a recess in housing 132, such as recess 190 of FIG. 4.

At 304, a sinter paste is applied about a perimeter of opening 146, such sinter paste 200 disposed about opening 146 within recess 190 as illustrated by FIG. 6 for example. According to one embodiment, the sinter paste includes a fine powder of a biocompatible bonding material mixed with a binder material. According to one embodiment, the biocompatible bonding material is one of gold, platinum, palladium, or any alloy combination thereof.

At 306, a feedthrough device, characterized by the absence of a ferrule, is positioned on the sinter paste so as to cover opening 146 in housing 132, such as ferrule 150 being positioned on sinter paste 200 as illustrated by FIG. 6. According to one embodiment, opening 146, feedthrough 150, and sinter paste 200 are configured so that the feedthrough 150 overlaps opening 146 such that a finally formed sinter joint has a width at least one-fourth the width of feedthrough 150, such as illustrated by FIG. 3.

At 308, a low-temperature sintering process is performed by heating housing 132, feedthrough 150, and sinter paste 200 to a temperature below the β-transus temperature of titanium for a desired duration to form finished sinter joint 180 from sinter paste 200, such as illustrated and described by FIG. 8 and the finished sinter joint 180 of FIG. 4, for example. According to one embodiment, the low-temperature sintering process is performed in an oven having a controlled environment. According to one embodiment, the low-temperature sintering process includes compressing the sinter paste while being heated.

In view of the above, according to the techniques and embodiments of the present disclosure, the attachment of feedthrough 150 to housing 132 using sinter joint 180 eliminates the need for a ferrule (such as ferrule 56 of FIG. 2). By directly integrating feedthrough 150 to housing 132 via sinter joint 180, as opposed to conventional techniques which integrate the feedthrough to the housing using a ferrule, the shortcomings associated with such a ferrule (e.g. brazed/welded joint, machining requirements, costs) are eliminated. When combined with the use of cermet for conductive elements 154, feedthrough 150 of the present disclosure provides a complete feedthrough 150 for implantable medical device 130 which is completely devoid of welds and/or brazing.

Also, by using a sintering process as described herein to attach feedthrough 150 to the titanium of housing 132 at temperatures below the β-transus temperature of titanium, grain growth within the titanium material of housing 132, particularly about a perimeter of opening 146, is greatly reduced relative to conventional techniques which employ high-temperature brazing or welding processes to attach feedthrough devices to housings via a ferrule. As described above, an average grain size of commercially pure titanium employed by housing 132 is initially in the range of about 10-40 μm.

According to one embodiment, attaching feedthrough 150 to housing 132 with a sinter joint 180 formed in accordance with the present disclosure results in an average grain size of the titanium of housing 132 proximate to opening 132 that does not exceed 100 μm. As such, according to one embodiment, implantable medical device 130 according to the present disclosure, such as that illustrated by FIGS. 3-5, is characterized by a titanium housing 132 having the distinctive structural characteristic imparted by the sintering process described herein of an average grain size not exceeding 100 μm, at least in a region of the housing directly proximate to opening 146. Such a characteristic is distinctive relative to joints formed by conventional techniques, such as welding and brazing, which result in average grain sizes greatly exceeding 100 μm, such as greater than 300 μm, for example.

By reducing the grain growth of the titanium of housing 132, dimensional distortions of housing 132 are also reduced as compared to conventional techniques, at least to levels whereby dimensions of opening 132 remain within design tolerances after attachment of feedthrough 150. According to one embodiment, dimensional changes of housing 132 do not exceed 5% relative to initial dimensions. As an example, if opening 146 is a rectangular opening having initial dimensions of 0.020"×0.040" prior to attachment of feedthrough 150, the dimensions after attachment using the sintering processes described herein will be within a range 0.019-0.021"×0.038-0.042". The reduced grain growth also results in the titanium of housing 132, particularly in the region immediately about the perimeter of housing 132, becoming less flexible and remaining more rigid as compared to conventional attachment techniques. Reducing dimensional distortions and retaining the rigidity of the titanium about opening 146 reduces the likelihood of a defective or failed connection of feedthrough 150 to housing 132.

Also, because of the low temperatures employed by the sintering process described herein, dimensional changes in housing 132 as a whole are also minimal. The housings of implantable medical devices, such as housing 132 of implantable medical device 130, are typically formed from two "halves" (one of the halves including opening 146) which are later joined to one another, typically by laser welding, to form complete housing 132. In order to achieve a hermetic seal, the two halves are required to be in close contact with one another during the laser welding process. For example, the dimensional profiles of the two halves of the housing are typically required to be held within a tolerance of +/−0.004". The low-temperatures associated with the sintering process described herein ensure that the dimensional profiles of the housing halves remain within required tolerances.

Finally, because sintering is a low-temperature process whereby the boundaries of the powdered metal particles fuse together to form a solid body in the absence of melting, a sinter joint typically includes gaps or voids within the solid body. In contrast, in joints formed by welding or brazing the bonding material is completely melted and reflows such that the resulting solid joint has virtually no voids or gaps. As a result, whereas a joint formed by brazing or welding has a density of greater than 99% (i.e. the joint comprises greater than 99% bonding material), a joint formed by sintering as described herein has a density of 90-99% (i.e. the joint comprises 90-99% bonding material, the remainder being gaps or voids).

For example, a brazed joint of pure gold would have a density of greater than 19.1 g/cm$^3$ (i.e. the density of pure being 19.3 g/cm$^3$), while a sinter joint of pure gold would have a density in the range of about 17.4-19.1 g/cm$^3$. As such, according to one embodiment, implantable medical device 130 according to the present disclosure, such as that illustrated by FIGS. 3-5, is characterized by a distinctive structural characteristic imparted by the sintering process of sinter joint 180 having a 90-99% density of bonding material (e.g. gold, gold alloy). It is noted that even though a sinter joint is less dense than a welded or brazed joint, sinter joint 180 still provides a hermetical seal between the feedthrough 150 and housing 132.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of the specific embodiments discussed herein. Therefore, it is intended that this invention be limited only by the claims and the equivalents thereof.

What is claimed is:

1. An implantable medical device comprising:
   a housing having an opening with an opening width;
   a feedthrough including an insulator having a bottom surface facing an interior space within the housing, a top surface facing away from the interior space, and opposing first and second side surfaces and having an insulator width between opposing side surfaces that is greater than the opening width; and
   a sinter joint between at least one of the bottom surface, top surface, and side surfaces of the insulator and the housing which hermetically seals the insulator directly to the housing without an intervening ferrule, braze or weld;
   wherein the housing comprises titanium, and wherein the titanium has an average grain size of not more than 100 µm.

2. The implantable medical device of claim 1, wherein the sinter joint comprises one of gold, palladium, iridium, and alloy combinations thereof.

3. The implantable medical device of claim 1, wherein a surface of the insulator at the sinter includes a metallized layer.

4. The implantable medical device of claim 1, wherein the sinter joint has a density in a range from 90 to 99 percent of a biocompatible bonding material.

5. The implantable medical device of claim 1, wherein a width of the sinter joint between the insulator and the housing along a perimeter of the housing opening is at least one quarter a width of the insulator at its widest point.

6. The implantable medical device of claim 1, wherein a plane normal to the opening passes through the housing, the sinter joint, and the insulator.

7. The implantable medical device of claim 1, wherein the sinter joint has a thickness in a direction perpendicular to the housing in a range from 25 to 200 µm.

8. The implantable medical device of claim 1, wherein the housing includes a flange which forms a recess that extends toward the interior space and about the opening, and the insulator being positioned at least partially within the recess and over the opening.

9. The implantable medical device of claim 8, wherein the flange includes first and second downwardly angled portions that forms opposing sidewalls of the recess and wherein opposing side surfaces of the insulator are respectively sealed to the opposing sidewalls of the recess.

10. An implantable medical device comprising:
    a housing having an opening with an opening width;
    a feedthrough including an insulator having a bottom surface facing an interior space within the housing, a top surface facing away from the interior space, and opposing first and second side surfaces and having an insulator width between opposing side surfaces that is greater than the opening width; and
    a sinter joint between at least one of the bottom surface, top surface, and side surfaces of the insulator and the housing which hermetically seals the insulator to the housing without an intervening ferrule;
    wherein the housing comprises titanium, and wherein the titanium has an average grain size of not more than 100 µm.

11. The implantable medical device of claim 10, wherein the sinter joint comprises gold.

12. The implantable medical device of claim 10, wherein in the sinter joint comprises one of gold, palladium, iridium, and alloy combinations thereof.

13. The implantable medical device of claim 10, wherein the sinter joint has a density in a range from 90 to 99 percent of a biocompatible bonding material.

14. The implantable medical device of claim 10, wherein a width of the sinter joint between the insulator and the housing along a perimeter of the housing opening is at least one quarter a width of the insulator at its widest point.

15. The implantable medical device of claim 10, wherein a plane normal to the opening passes through the housing, the sinter joint, and the insulator.

16. The implantable medical device of claim 10, wherein the sinter joint has a thickness in a direction perpendicular to the housing in a range from 25 to 200 μm.

17. The implantable medical device of claim 10, wherein the housing includes a flange which forms a recess that extends toward the interior space and about the opening, and the insulator being positioned at least partially within the recess and over the opening.

* * * * *